US012690881B2

(12) United States Patent
Ettwein et al.

(10) Patent No.: US 12,690,881 B2
(45) Date of Patent: Jul. 28, 2026

(54) MEDICAL INSTRUMENT AND METHOD FOR THE MANUFACTURE OF A MEDICAL INSTRUMENT

(71) Applicant: Aesculap AG, Tuttlingen (DE)

(72) Inventors: Pierre Ettwein, Engen (DE); Sven Barthelmes, Emmingen-Liptingen (DE); Maciej Cynka, Miedzichowo (PL); Mateusz Hoffmann, Nowy Tomysl (PL)

(73) Assignee: Aesculap AG, Tuttlingen (DE)

( * ) Notice: Subject to any disclaimer, the term of this patent is extended or adjusted under 35 U.S.C. 154(b) by 99 days.

(21) Appl. No.: 18/911,372

(22) Filed: Oct. 10, 2024

(65) Prior Publication Data

US 2025/0032140 A1 Jan. 30, 2025

Related U.S. Application Data

(63) Continuation of application No. PCT/EP2023/059372, filed on Apr. 11, 2023.

(30) Foreign Application Priority Data

Apr. 12, 2022 (EP) .................................... 22167964

(51) Int. Cl.
A61B 17/28 (2006.01)
A61B 17/00 (2006.01)
A61B 17/3201 (2006.01)

(52) U.S. Cl.
CPC ...... *A61B 17/2816* (2013.01); *A61B 17/3201* (2013.01); *A61B 2017/00477* (2013.01);
(Continued)

(58) Field of Classification Search
CPC .... A61B 2017/2926; A61B 2017/2927; A61B 2017/2931; A61B 2017/2933;
(Continued)

(56) References Cited

U.S. PATENT DOCUMENTS 3,735,763 A 5/1973 Shannon et al.
5,478,347 A 12/1995 Aranyi
(Continued)

FOREIGN PATENT DOCUMENTS

JP 3159703 U 5/2010

OTHER PUBLICATIONS

Office Action received in European Application No. 22 167 964.0-1113 dated Apr. 28, 2025, 6 pages.
(Continued)

*Primary Examiner* — Majid Jamialahmadi
(74) *Attorney, Agent, or Firm* — Christopher A. Rothe; CM Law

(57) ABSTRACT

A medical instrument has a first part connected to a second part with a connecting element. The first and second parts are pivotable relative to one another about a pivot axis defined by a longitudinal axis of the connecting element. The first part has a first bearing area, and the second part has a second bearing area. The first bearing area and second bearing area face each other. In a mounted state, a biasing element is arranged between the first and second bearing areas. The biasing element, in the mounted state, is held in a compressed state between the first and second bearing areas by the connecting element so as to exert a biasing force on the first and second bearing areas to keep them biased away from one another.

16 Claims, 12 Drawing Sheets

(52) U.S. Cl.
CPC ............... *A61B 2017/00526* (2013.01); *A61B 2017/2808* (2013.01)

(58) Field of Classification Search
CPC .... A61B 2017/2934; A61B 2017/2936; A61B 2017/2938; A61B 2017/2939; A61B 2017/2943; A61B 2017/2837; A61B 2017/2945; A61B 2017/2932; A61B 2017/2947; A61B 17/2816; A61B 17/32; A61B 17/2812; A61B 17/3201; A61B 17/28; A61B 17/2804; A61B 17/29; A61B 2018/1457; A61B 2018/146; B25B 27/205
See application file for complete search history.

(56) References Cited

U.S. PATENT DOCUMENTS

| | | | |
|---|---|---|---|
| 9,987,078 | B2 | 6/2018 | Thomson et al. |
| 2008/0167651 | A1* | 7/2008 | Tetzlaff .............. A61B 18/1442 606/51 |
| 2009/0287235 | A1 | 11/2009 | Fortier et al. |

OTHER PUBLICATIONS

Search Report received International Application No. PCT/EP2023/059372 dated Jun. 19, 2023, 3 pages.
Wikipedia, https://en.wikipedia.org/wiki/Washer_(hardware), "Washer (hardware)", Jan. 11, 2022, 23 pages.
Written Opinion received International Application No. PCT/EP2023/059372 filed Jun. 19, 2023, 7 pages.

* cited by examiner

FIG.5
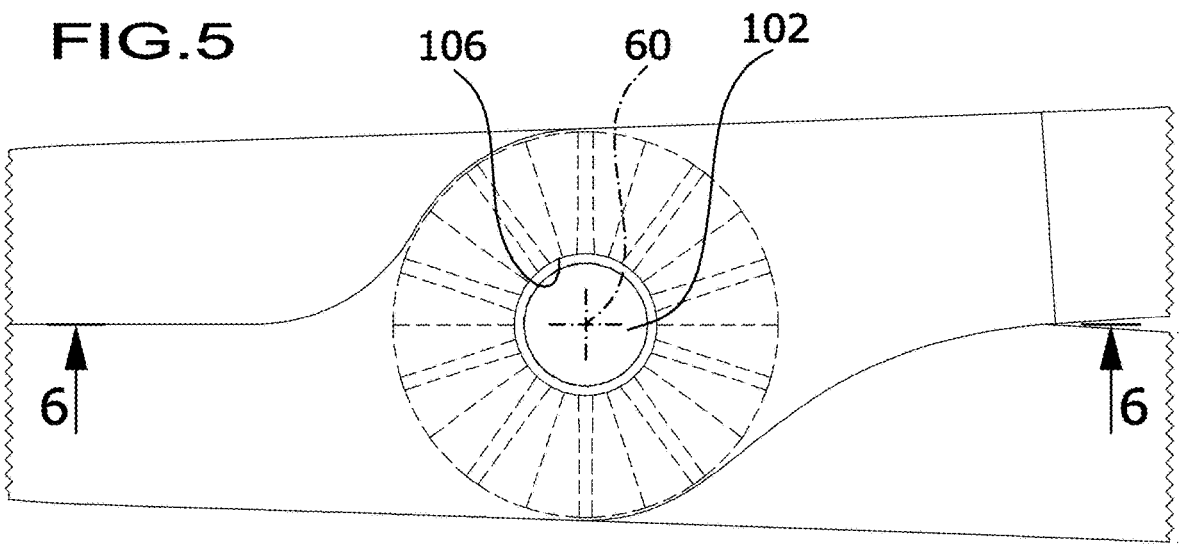
FIG.6
FIG.7
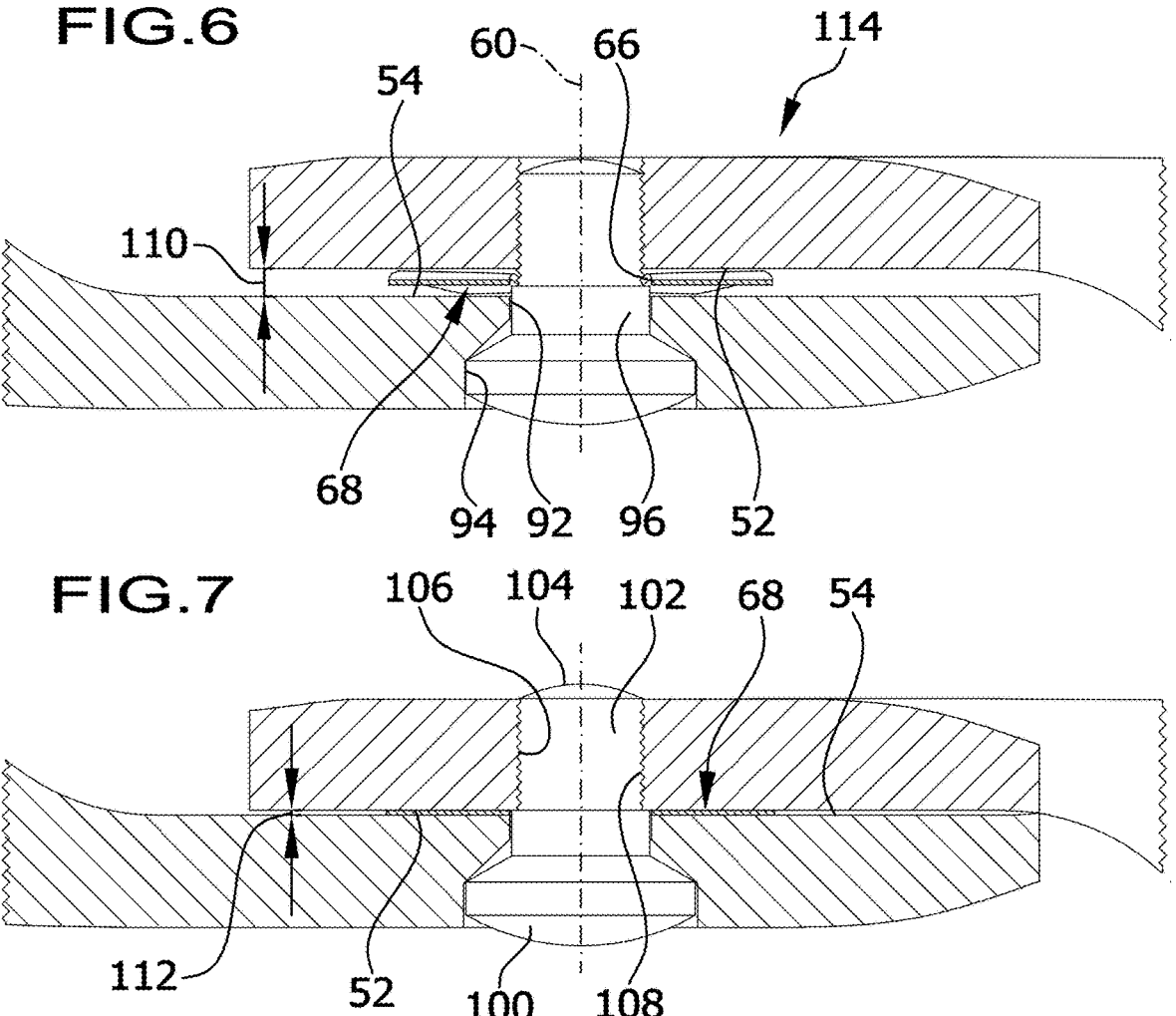

FIG.8
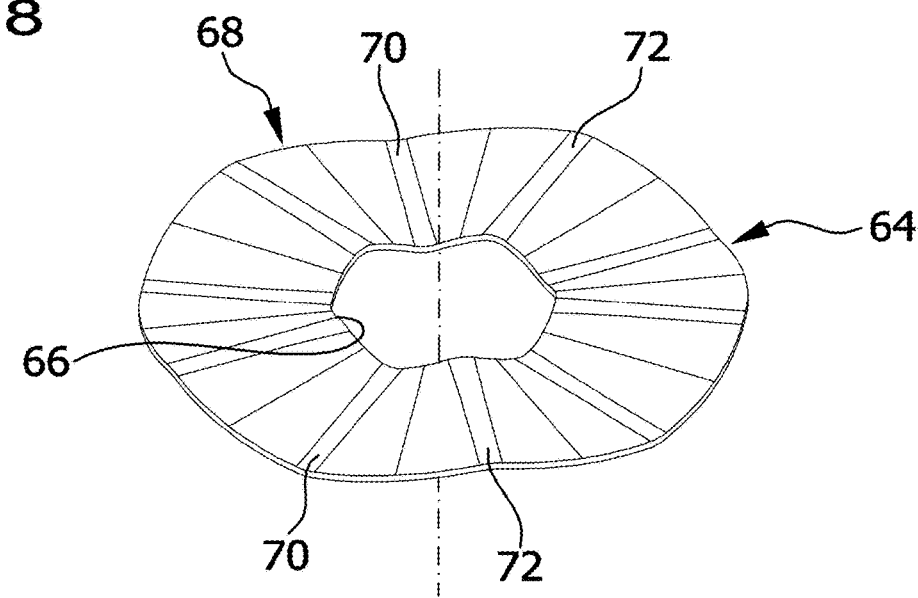
FIG.9
FIG.10
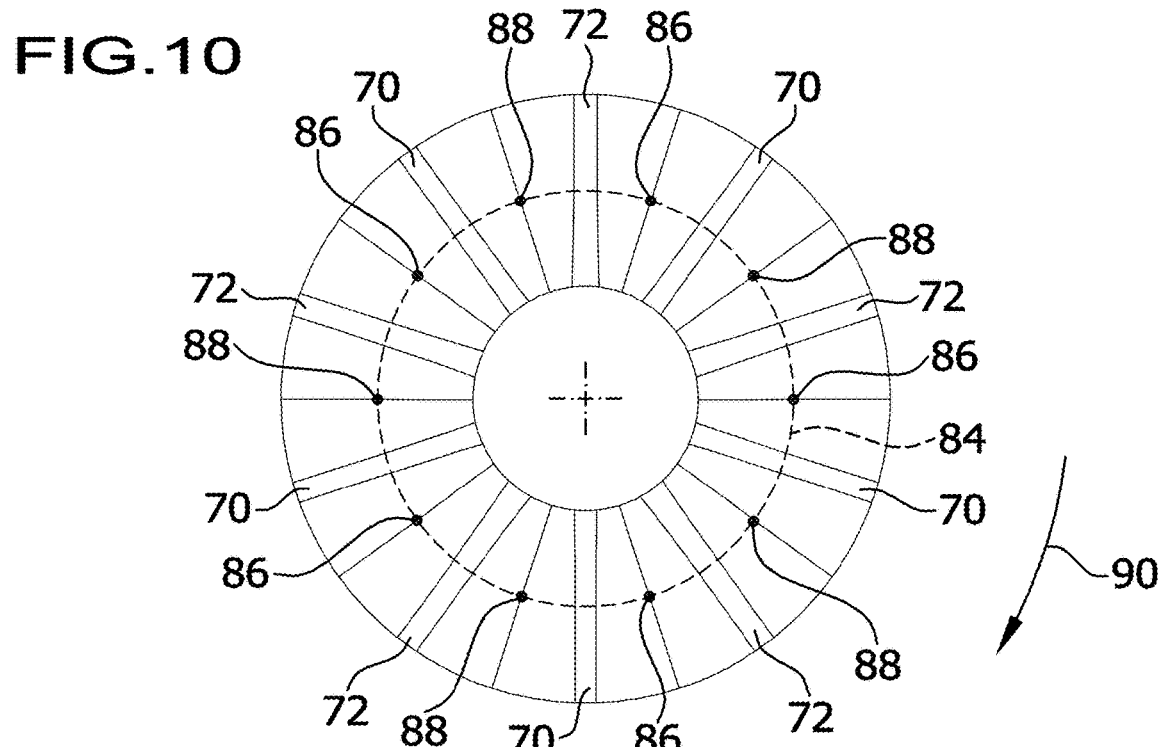

MEDICAL INSTRUMENT AND METHOD FOR THE MANUFACTURE OF A MEDICAL INSTRUMENT

CROSS-REFERENCE TO RELATED APPLICATIONS

This application is a continuation under 35 U.S.C. § 365(c) of International Application No. PCT/EP2023/ 059372, filed on Apr. 11, 2023, and claims priority to European Application No. 22167964.0, filed on Apr. 12, 2022. The contents of International Application No. PCT/ EP2023/059372 and European Application No. 22167964.0 are incorporated by reference herein in their entireties.

FIELD

The present disclosure relates to a medical instrument comprising a first part and a second part which are connected to one another with a connecting element so as to be pivotable relative to one another about a pivot axis defined by a longitudinal axis of the connecting element, wherein the first part has at least one first bearing area,
wherein the second part has at least one second bearing area, and wherein the at least one first bearing area and the at least one second bearing area are arranged so as to face each other.

Further, the present disclosure relates to a method for the manufacture of a medical instrument, the medical instrument comprising a first part and a second part, the first part having at least one first bearing area, the second part having at least one second bearing area, the method further comprising:
arranging the at least one first bearing area and the at least one second bearing area such that they face each other, and connecting the first part and the second part to one another with a connecting element such that the first and second parts are pivotable relative to one another about a pivot axis defined by a longitudinal axis of the connecting element.

BACKGROUND

Medical instruments, also called surgical instruments, are known for their high degree of precision. Different types of such instruments are commonly used, for example pliers, nippers, clamps, needle holders or scissors. For such instruments, a joint defined by the connecting element, which connects the first and second parts of the instruments, said joint being free of play and having a smooth motion, is regarded as pleasant by surgeons. Such a handling of an instrument gives a reasonable impression of the quality of such an instrument.

Instruments described at the outset are manufactured by connecting the two parts together with the connecting element. The instrument is adjusted with the connecting element, which is predominantly used in the form of a screw. During the manufacture of the instrument, the motion force of the joint of the instrument is adjusted by the pretension of the two parts, also called arms or branches of the instrument, against each other.

However, after several applications of the instrument by a user, wear occurs on the first and second bearing areas, also called running surfaces of the instrument joint. This effect increases when the joint is not oiled after reprocessing of the instrument. Reprocessing in this sense means subjecting the instrument a washing and sterilization cycle.

Due to the wear, play can occur in the joint, and the motion force perceptible by a user during use gets lost.

SUMMARY

Therefore, it is an object of the present disclosure to provide improved medical instruments, in particular having an improved durability.

This object is achieved in accordance with the present disclosure in a medical instrument described in the outset in that, in a mounted state, a biasing element is arranged between the at least one first bearing area and the at least one second bearing area, and in that the biasing element, in the mounted state, is held in a compressed state between the at least one first bearing area and the at least one second bearing area by the connecting element so as to exert a biasing force on the at least one first bearing area and the at least one second bearing area for keeping them biased away from one another.

Providing a medical instrument as proposed by the present disclosure with a biasing element has, in particular, the advantage that the problem of a lost motion force is no longer an issue. The biasing element arranged between first and second bearing areas or between the cooperating running surfaces of the first and second part of the instrument are no longer subject to wear as is the case for instruments without the proposed biasing element. Wear, as already set forth above, has a negative influence on the quality of the instrument. Rather, the biasing element arranged between the first and second bearing areas causes a steady and long-lasting motion force over the complete motion range of the medical instrument, also referred to as an opening angle of the pivotally coupled first and second parts. The adjustability of the medical instrument, in particular the joint motion during assembly, is improved, due to the biasing element with a small suspension travel. In addition, the precision of the instrument as a whole, in particular the jaws or working ends defined by cooperating working elements, during surgical operations is improved, when there is no play between the first and second parts of the medical instrument. In other words, wear that occurs with known standard medical instruments during use is compensated by the biasing element. If the proposed improved medical instruments are adjusted during their manufacture such that the biasing element exerts a biasing force on the at least one first and second bearing areas, i.e. on the two parts of the medical instruments, the adjustment is maintained due to the biasing property of the biasing element in the mounted state, in which it is held compressed between the first and second bearing areas.

Preferably, the biasing element is configured in the form of a spring washer having a central opening for receiving the connecting element, and the biasing element is arranged so as to surround the pivot axis. Such a configuration allows for a simple assembly of the medical instrument. The biasing element can easily be mounted with a connecting element in the form of a screw or rivet by putting the screw or rivet through the central opening of the spring washer. Thus, the spring washer can be securely held in place and cannot get lost during use of the instrument. Further, a spring washer is well suited for exerting a biasing force on the first and second parts of the medical instrument.

It is advantageous if the spring washer is configured in the form of a wave washer. A wave washer in this sense is a spring washer having an undulated shape, preferably with several points or lines of inflections which define a changing curvature of the wave washer. Thus, the wave washer actually comprises several portions that have a biasing effect. Therefore, even if one wave of the wave washer is damaged and no longer functions as a biasing element, the remaining waves or biasing portions of the wave washer can still maintain the desired property of the wave washer. Further, a wave washer can be compressed to a substantially flat configuration while still having the desired biasing property. This is typically not achievable with a Belleville washer.

According to a preferred embodiment, the wave washer, in particular in an initial state in which it is separate from the first and second bearing areas and does not exert any spring force, has a wavelike shape defining at least one wave trough and at least one wave crest. In particular, the wave washer can have a plurality of wave troughs and a plurality of wave crests. As already described above, a plurality of such waves defined by wave troughs and wave crests provides improved biasing properties of a wave washer compared to a Belleville washer.

The spring washer can be manufactured in a simple manner if the wave washer has a constant or substantially constant thickness. This allows for the manufacture of the wave washer from a sheet material by squeeze molding.

Preferably, the wave washer undulates in a circumferential direction with respect to the pivot axis. This means that the wave crests and wave troughs extend in radial direction. In other words, the wave washer has a wavelike structure which is visible from a side thereof.

It is also advantageous, if the spring washer undulates in a radial direction with respect to the pivot axis. This means that waves are provided in a radial direction leading to maxima and minima of waves, i.e. wave troughs and wave crests extending in circumferential direction.

Further, it is favorable if a cutting line of the wave washer in a radial or circumferential direction with respect to the pivot axis has at least two points of inflection, in particular three, four, five, six, seven, or more points of inflection. As already mentioned above, a point of inflection in a mathematical sense means that a curvature changes at the point of inflection. For example, a concave shape changes to a convex shape at the point of inflection. In other words, a wave washer with such a configuration has at least two changes of its curvature in circumferential or radial direction. The more points of inflection that are defined by the spring washer configuration, the more so-called biasing portions of the spring washer are defined having the advantages set forth above.

In accordance with a preferred embodiment, the wave washer has a first surface and a second surface, the first and second surfaces facing in opposite directions, the first surface defines a first contact plane of the wave crests, and the second surface defines a second contact plane of the wave troughs. Such a wave washer has the advantage that several points or lines of contact are defined between the wave washer and the respective first and second bearing surfaces of the first and second parts of the instrument. Thus, biasing forces can more or less be evenly distributed along the circumference of the wave washer.

The wave washer can be manufactured in a simple manner if the first contact plane and the second contact plane extend in parallel or substantially in parallel to one another. This property can, in particular, apply in the initial state and/or in the mounted state. Such a configuration allows for adjusting the first and second parts of the instrument in a connecting region of the instrument in the vicinity of the connecting element in parallel.

Further, it is advantageous if the first contact plane and the second contact plane define a first distance from one another in the initial state, if the first contact plane and the second contact plane define a second distance from one another in a mounted state in which the biasing element is mounted between the at least one first bearing area and the at least one second bearing area, and if the first distance is greater than the second distance. This defines, in particular, that the wave washer is in a compressed state in the mounted state so that it can long-lastingly exert a biasing force on the first and second bearing areas for maintaining the desired motion force of the instrument.

Preferably, in the mounted state, the second distance has a maximum value of about 1.2 times the thickness of the wave washer, in particular, of about 1.1 times the thickness of the wave washer. In other words, the wave washer has a substantially flat configuration in the mounted state if the ratio between the second distance and the thickness of the wave washer is within the defined ranges.

Further, it is favorable if, in the initial state, the first distance has a value in a range from about 2 times the thickness of the wave washer to about 10 times the thickness of the wave washer. In particular, this value can be in a range from about 2 times the thickness of the wave washer to about 5 times the thickness of the wave washer. This configuration defines the height and the depth of the wave crests and the wave troughs in the initial state and therefore also the biasing properties of the wave washer. Consequently, a wave washer best suited for the respective medical instrument can be chosen for exerting the desired motion force of the medical instrument.

In accordance with the embodiment, the connecting device is configured in the form of an applied connecting device comprising one single first bearing area and one single second bearing area, and the first part with the single first bearing area is applied to the single second bearing area with the biasing element arranged therebetween. A medical instrument with such a connecting device can be easily assembled as the first part of the instrument can be provided, the biasing element can be set on the first bearing area and the second part of the instrument can be set with its second bearing area on the biasing element. Then, the three components can be connected together with the connecting element, for example a screw or a rivet.

In order to obtain a medical instrument with an improved stability in the region of the connecting element, it is advantageous if the connecting device is configured in the form of a box-type connecting device, if the first part has a female connecting portion with a through opening, if the second part has a male connecting portion, and if, in the mounted state, the male connecting portion extends through the through opening. Such a box-type connecting device provides for the guidance of the second part of the instrument by the first part as there are two cooperating bearings between the first and second part, namely on both sides of the male connecting portion.

In particular with a box-type connecting device, it is advantageous if the female connecting portion has two first bearing areas facing each other and if the male connecting portion has two second bearing areas facing away from one another. Thus, two separate bearings can be defined with such a medical instrument, i.e. an instrument having a connecting device in the form of a box-type connecting device.

In order to provide medical instruments of different types, it is favorable if the first part has a first distal end, if the second part has a second distal end, if a first tool element is formed or arranged on the first distal end, if a second tool element cooperating with the first tool element is formed or arranged on the second distal end, and if the first tool element and the second tool element form a medical tool. Thus, depending on the type of the respective tool elements, a desired medical tool can be formed. In particular, the tool elements can be configured in the form of clamping jaws, or gripping jaws or cutting edges so that medical tools in the form of clamps, grips, grasping forceps or scissors can be made.

Moreover, in accordance with a further preferred embodiment, provision can be made that the first part has a first proximal end, that the second part has a second proximal end, that a first holding element is formed or arranged on the first proximal end, and that a second holding element is formed or arranged on the second proximal end. Such holding elements provide for an easy handling of the medical instrument by a user. In particular, the first and second holding elements can be configured in the form of rings. This allows a user to securely hold the medical instrument by introducing at least one finger through each ring.

Preferably, the medical tool is configured in the form of a pair of scissors, a needle holder, or a clamp. Thus, the improved properties of the proposed medical instrument having a biasing element arranged between the first and second bearing areas can advantageously be used in connection with different types of medical instruments.

The manufacture of a medical instrument becomes simple and an adjustment of the instrument rather easy if the connecting element is configured in the form of a screw or rivet. In particular, a screw can be used for fine adjustment of the desired motion force by more or less compressing the biasing element between the first and second bearing areas of the first and second parts of the instrument.

The object as set forth at the outset is further achieved in a method described at the outset in that the method further comprises: arranging a biasing element between the at least one first bearing area and the at least one second bearing area before connecting the first part and the second part to one another, compressing the biasing element with the first and second parts in a compressed state, and maintaining the compressed state by adjusting the connecting element such that the biasing element enduringly exerts a biasing force on the at least one first bearing area and the at least one second bearing area for keeping them biased away from one another.

The proposed improved method for the manufacture of a medical instrument allows for a simple adjustment thereof. As the biasing element is compressed during the manufacture, i.e. the assembly of the instrument, from the initial state to a compressed state, it enduringly exerts a desired biasing force on the two parts of the medical instrument. Any wear will be compensated by the biasing element. Further, the proposed method also has the advantage that any deformation of the two parts of the medical instruments, in particular their respective bearing areas during the manufacture of the two parts or any manufacturing tolerances, can easily be compensated with the biasing element. Therefore, the proposed method can, in particular, also be performed completely automatically, i.e. by a machine. In other words, the proposed method for the manufacture of a medical instrument allows for producing the instrument by a machine. Generally, an adjustment by hand is no longer necessary.

Further, use of a wave washer as a biasing element in a method described above or as a biasing element in any of the above-described embodiments of the medical instrument is proposed.

BRIEF DESCRIPTION OF THE DRAWINGS

The following description of preferred embodiments serves, in conjunction with the drawing figures, for a more detailed explanation of the present disclosure.

FIG. 5 shows a partially broken plan view of the arrangement in FIG. 4 in the region of the connecting device;

FIG. 6 shows a sectional view taken along line 6-6 in FIG. 5 before adjusting the instrument;

FIG. 7 shows a view similar to the arrangement in FIG. 6 with the biasing element in the mounted state, i.e. compressed;

FIG. 8 shows a perspective view of the embodiment of a biasing element shown in FIGS. 1 to 7;

FIG. 9 shows a side view of the embodiment of the biasing element in FIG. 8;

FIG. 10 shows a top view of the biasing element shown in FIGS. 8 and 9;

DETAILED DESCRIPTION

Figure 1:
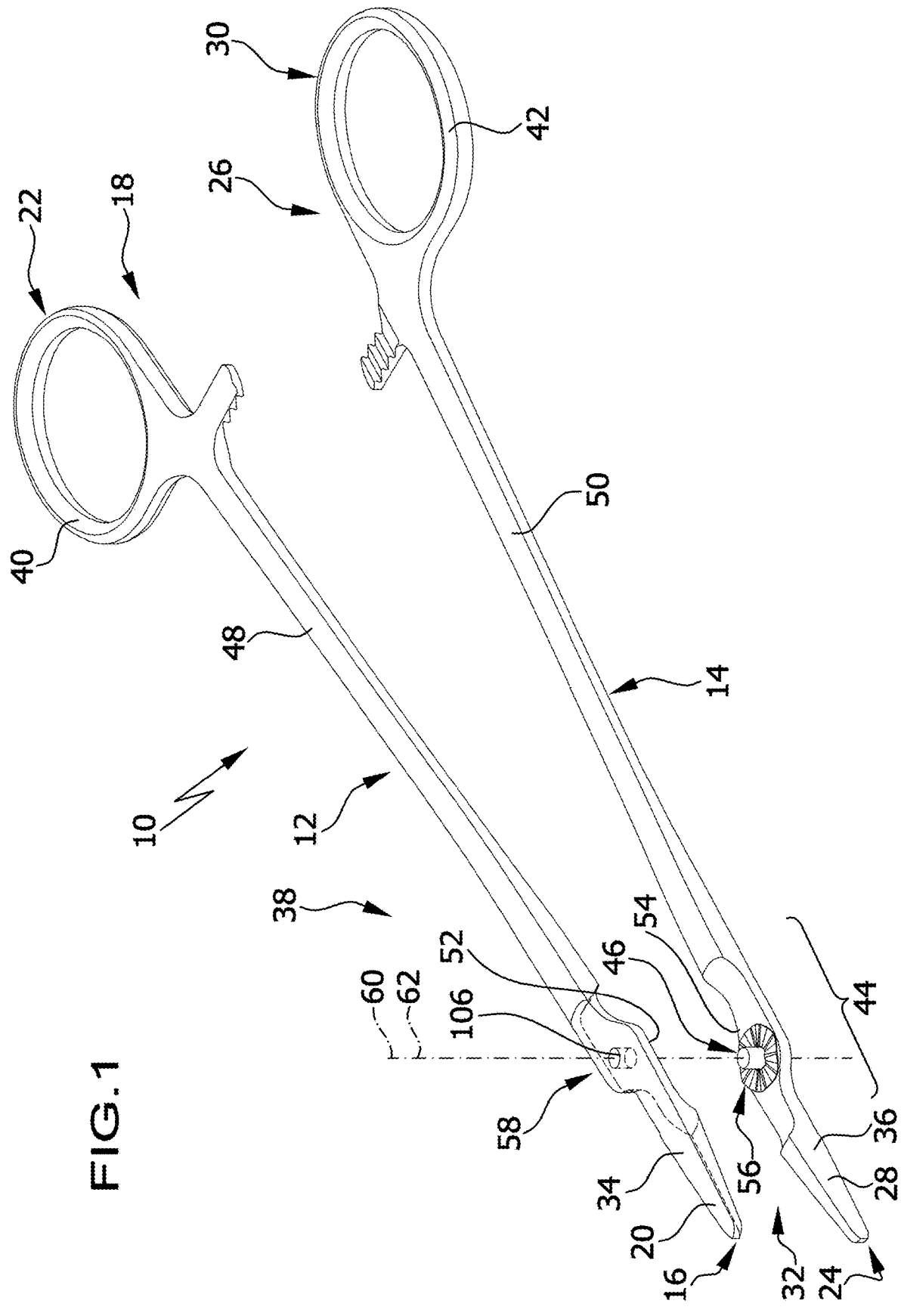
FIG. 1 shows a schematic exploded view of an embodiment of a medical instrument.
Figure 2:
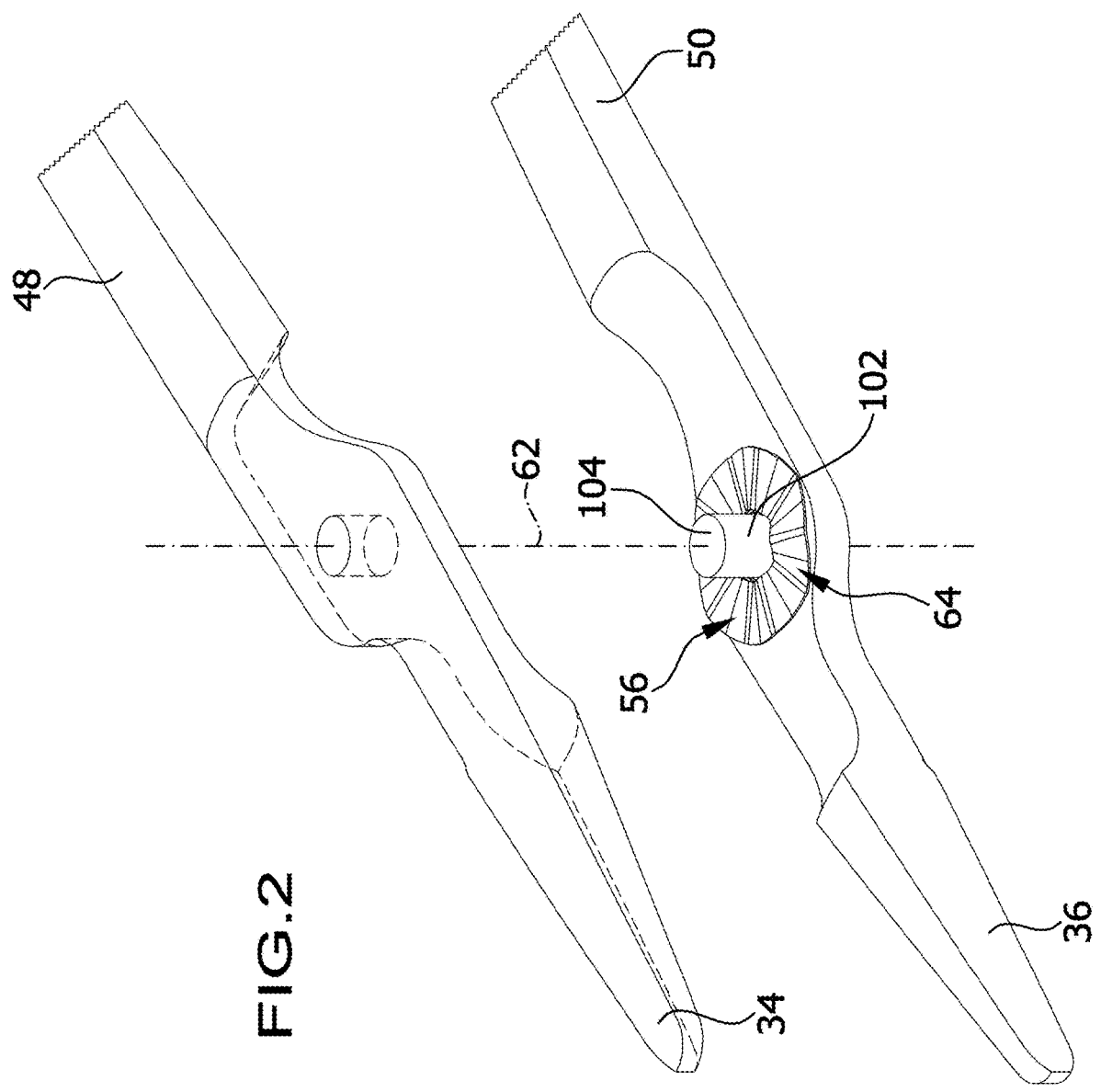
FIG. 2 shows an enlarged partial view of a distal end of the instrument depicted in FIG. 1.
Figure 3:
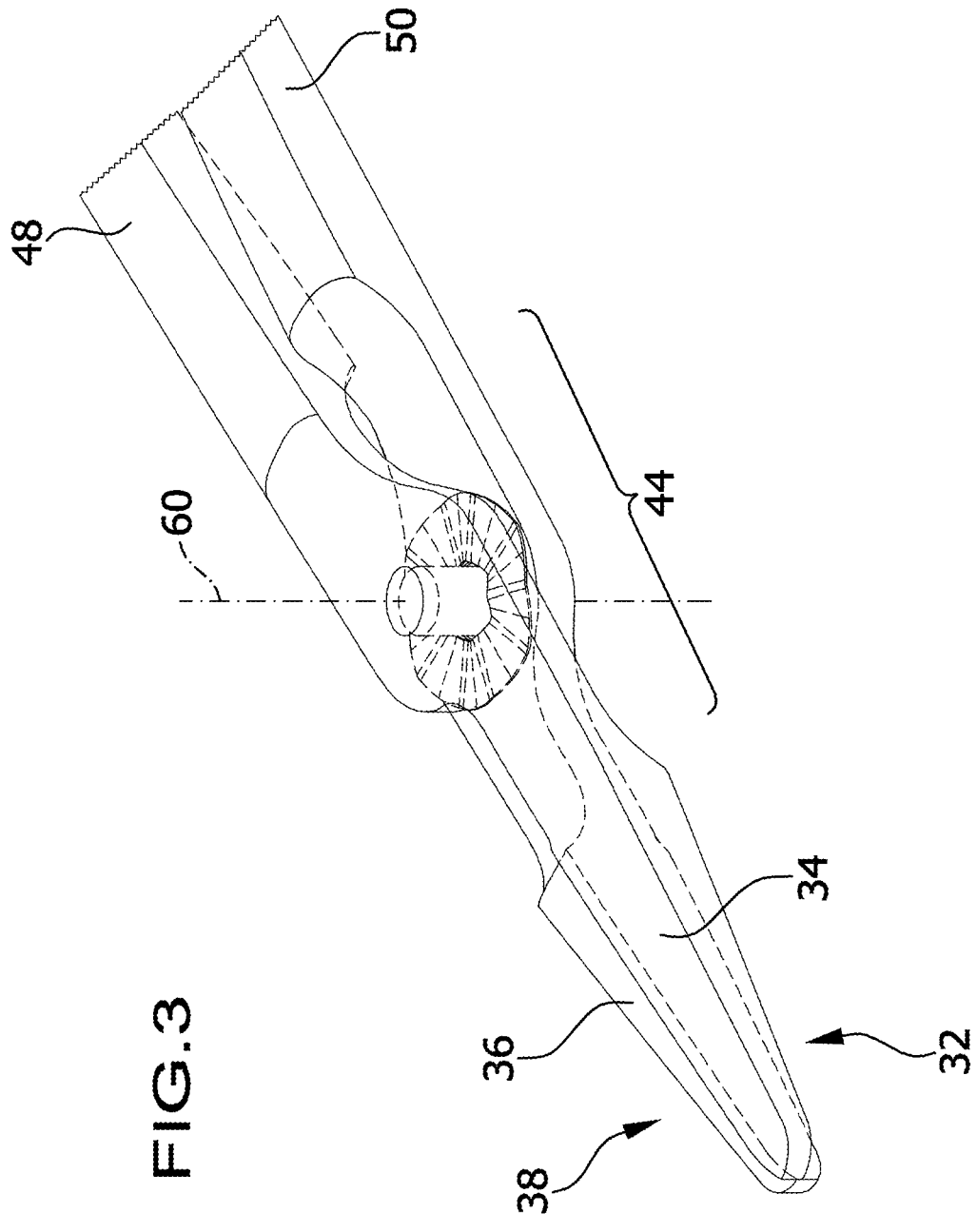
FIG. 3 shows a partially broken view of the arrangement in FIG. 2 before adjusting the connecting element, i.e. with the biasing element in the initial state.
Figure 4:
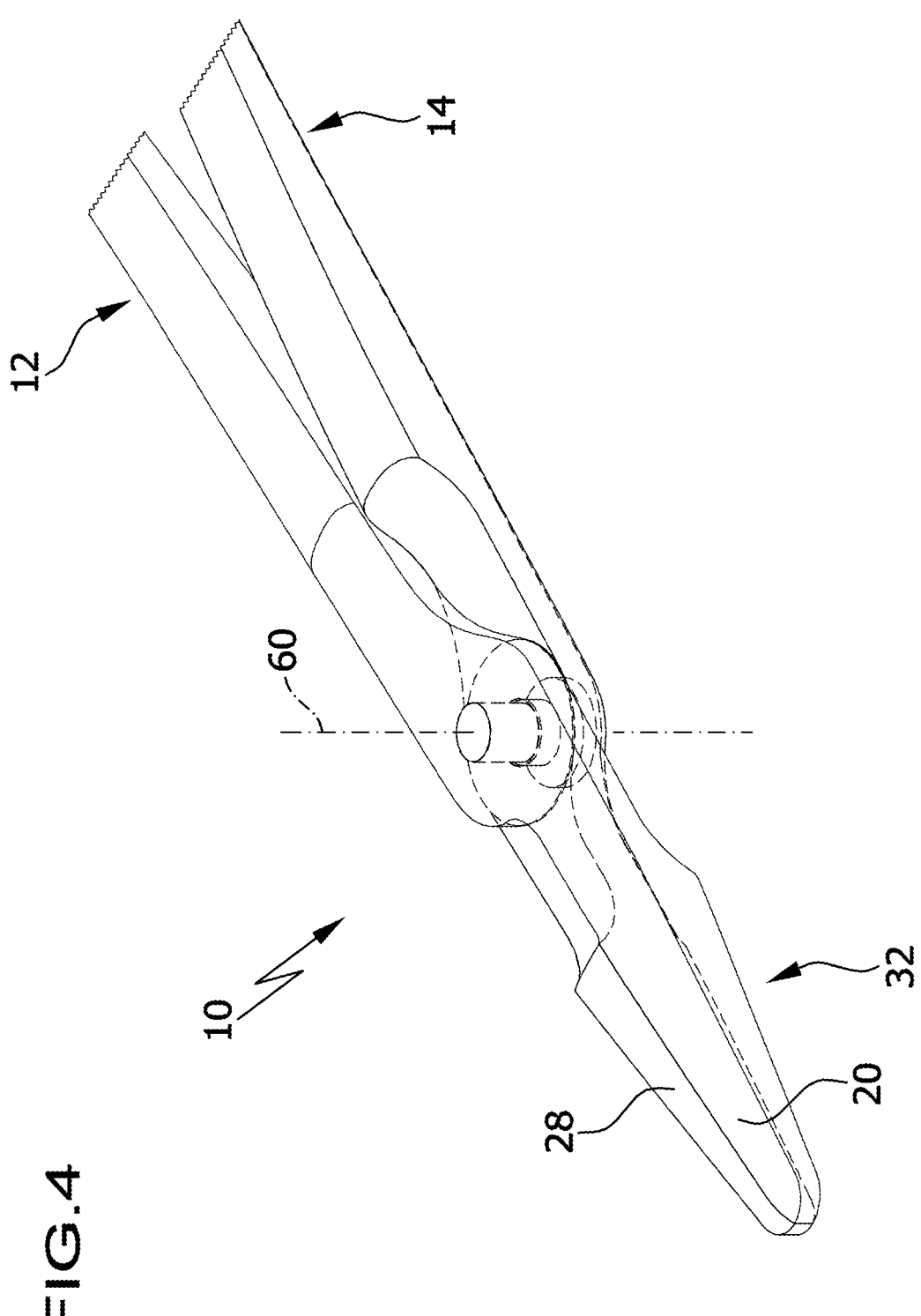
FIG. 4 shows a partially broken view of the arrangement in FIG. 3 in the mounted state, i.e. with the biasing element in the compressed state.

FIG. 1 shows a first embodiment of a medical instrument 10 in an exploded view. The instrument 10 comprises a first part 12 and a second part 14. The exploded view in FIG. 1 shows the instrument 10 during assembly.

The first part 12 has a first distal end 16 and a first proximal end 18. A first tool element 20 is formed or arranged on the first distal end 12. Further, a first holding element 22 is formed or arranged on the first proximal end 18.

In a similar manner as described in connection with the first part 12, the second part 14 has a second distal end 24 and a second proximal end 26. A second tool element 28 configured for cooperating with the first tool element 20 is formed or arranged on the second distal end 24. Moreover, a second holding element 30 is formed or arranged on the second proximal end 26.

The first tool element and the second tool element 28 form or define a medical tool 32.

In the embodiment of the medical instrument 10 shown in FIGS. 1 to 7, the first and second tool elements 20, 28 are configured in the form of clamping jaws 34, 36 so that the medical instrument 10 as a whole is configured in the form of a medical clamp 36.

The first and second holding elements 22, 30 are configured in the form of rings 40, 42 commonly used with such standard medical instruments for an easy handling by a surgeon or another user.

In alternative embodiments not shown in the drawing figures, the first and second tool elements 20 are made in the form of cooperating cutting edges so that the medical tool 32 is configured in the form of a pair of scissors.

In a further embodiment not depicted in the drawing figures, the medical tool 32 is configured in the form of a needle holder which has structured gripping phases.

The first and second parts 12, 14 are connected to one another in a connecting region 44 by a connecting element 46. The embodiment of the medical instrument 10 shown in FIG. 1 has elongated arms 48, 50, also called branches, which extend between the connecting region 44 and the respective proximal ends 18, 26.

Further, the first part 12 has a first bearing area 52. The second part 14 has a second bearing area 54. As shown in FIGS. 1 to 7, the first bearing area 52 and the second bearing area 54 are arranged so as to face each other.

In a standard medical instrument, the two parts 12 and 14 would be assembled so that the first and second bearing areas 52 and 54 would directly contact each other. The two parts 12 and 14 would be connected with a connecting element in the form of a screw or rivet so as to pivotably connect the two parts 12 and 14 to one another.

The main difference between the medical instrument 10 shown in FIGS. 1 to 7 and the described standard medical instrument is that the first and second bearing areas 52 and 54 are not in direct contact with one another. Rather, a biasing element 56 is arranged between the first and second bearing areas 52, 54.

The connecting region 44 comprises, in particular, the first and second bearing areas 52 and 54 and the connecting element 46, which together define a so-called connecting device 58. The connecting element 46 serves the purpose of pivotably connecting the first and second parts 12, 14 to one another so as to be pivotable about a pivot axis 60 defined by a longitudinal axis 62 of the connecting element 46.

The biasing element 56 is configured in the form of a spring washer 64 having a central opening 66 for receiving the connecting element 46. The configuration of the spring washer 64 further allows for the arrangement of the biasing element 56 so as to surround the pivot axis 60 as depicted, in particular, in FIGS. 5 and 6.

FIGS. 1 to 10 show an embodiment of a spring washer 64 in the form of a so-called wave washer 68. The wave washer 68 has a wavelike shape as shown, in particular, in FIGS. 8 to 10. Theses drawing figures show an initial state of the wave washer 68, in which it is separate from the first and second parts 12, 14. The wave washer 68 does not exert any spring force in this initial state.

The wavelike shape of the wave washer 68 defines several wave troughs 70 and several wave crests 72.

Further, the wave washer 68 of the embodiment depicted in drawing FIGS. 1 to 10 has a constant or substantially constant thickness 74.

The wave washer 68 depicted in the drawing FIGS. 1 to 10 undulates in a circumferential direction with respect to the pivot axis 60. This means that the curvature of the wave washer 68 changes in an alternating manner from a convex to a concave curvature and vice versa.

The wave washer 68 has a first surface 76 and a second surface 78. The first and second surfaces 76, 78 face in opposite directions. As depicted in FIG. 9, the first surface 76 defines a first contact plane 80 of the wave crests 72. The second surface 78 defines a second contact plane 82 of the wave troughs 70.

The first and second contact planes 80, 82 extend in parallel or substantially in parallel to one another. This is the case in the initial state as depicted in FIG. 9. It is also the case in the mounted state as described further below.

A cutting line 84 of the wave washer 68 in a circumferential direction defines several points of inflection 86 and 88, which are defined alternatingly along the circumference of the cutting line 84. With respect to the first surface 76 and with reference to FIGS. 8 to 10, adjacent points of inflection 86 and 88 define either a wave crest 72 or a wave trough 70 between them.

Looking at FIG. 10, moving along the cutting line 84 along its circumference in a clockwise direction 90 and starting at any point of inflection 86 follows a concave curvature of the wave washer 68 pointing away from the first surface 76 until the adjacent point of inflection 88 is reached, where the curvature changes from concave to convex with respect to the first surface 76. Further following the cutting line 84 in the clockwise direction 90 to the next point of inflection 86, the curvature remains substantially convex until the point of inflection 86 is reached. The described change of curvature of the cutting line 84 continues along its circumference. The described configuration results from the wave washer's shape undulating in a circumferential direction with respect to the pivot axis 60.

As already mentioned, FIG. 1 schematically shows the assembly of the medical instrument 10. The second part comprises a bore 92 with an enlarged region 94. Bore 92 is adapted to receive an unthreaded shaft portion 96 of the connecting element 46, which is configured in the form of a connecting screw 98. The region 94 is configured to receive a screw head 100 of the connecting screw 98.

A threaded shaft portion 102 extends between shaft portion 96 and a free end 104 opposite the screw head 100 of the connecting screw 98.

A bore 106 with inner threads 108 is provided on the first part 12 for receiving the threaded shaft portion 102.

For the assembly of the medical instrument 10, the connecting screw 98 is introduced with its free end 104 through bore 92 so that threaded shaft portion 102 projects beyond the second bearing area 54 as shown in FIG. 1.

The wave washer 68 is then placed over the threaded shaft portion 102 so that the second surface 78 contacts the second bearing area 54 as shown in FIG. 1.

Next, the first part 12 is brought into engagement with the connecting screw 98 by screwing the threaded shaft portion 102 into bore 106 with its inner threads 108, which correspond to the threaded shaft portion 102.

FIG. 6 shows a state during the assembly in which the wave washer 68 is still in the initial state, i.e. it does not exert any spring force as it is not deformed with respect to its initial state shown in FIGS. 8 to 10. However, the first surface 76 with the wave crests 72 is now in contact with the first bearing area 52.

In the initial state, the first contact plane 80 and the second contact plane 82 define a first distance 110 from one another. The distance 110 corresponds to the gap between the first and second bearing areas 52, 54 as shown in FIG. 6 as long as the wave washer 68 is in the initial state.

For adjusting the instrument 10, the connecting screw 98 is further screwed into bore 106, thereby compressing the wave washer 68 and transferring the same from the initial state to a compressed state. FIG. 7 shows a compressed state of the wave washer 68 in the mounted or assembled state of the medical instrument 10.

In this mounted state, the first contact plane 80 and the second contact plane 82 define a second distance 112 corresponding to the reduced gap between the first and second bearing areas 52, 54. As can be seen in FIGS. 6 and 7, the first distance 110 is greater than the second distance 112.

Further, the wave washer 68, i.e. the biasing element 56, is arranged between the first and second bearing areas 52, 54 in the mounted state, and it is held in the compressed state between them by the connecting element 46. Since the biasing element 56 is held compressed by the arrangement of the connecting device 58, it exerts a biasing force on the first and second bearing areas 52, 54 for keeping them biased away from one another.

The spring force exerted by the wave washer 68 on the parts 12 and 14 depends on its compression. The more it is compressed, the greater the spring force becomes. This allows for an individual adjustment of a motion force of the medical instrument 10 when the two parts 12, 14 are pivoted relative to one another about the pivot axis 60. The motion force is related to the friction between the parts 12 and 14 on the one hand and the biasing element 56 on the other hand.

In order to improve the cleanability of the medical instrument 10, it is preferably adjusted such that, in the mounted state, the second distance 112 has a maximum value of about 1.2 times the thickness 74 of the wave washer 68. In order to reduce recesses between the bearing areas 52 and 54 defined by the wave troughs 70 and the wave crests 72, the connecting screw 98 is adjusted such that the maximum value of the second distance 112 is about 1.1 times the thickness 74 of the wave washer 68.

Referring to FIG. 9, the first distance 110 in the initial state has a value in a range of about two times the thickness 74 of the wave washer 68 to about ten times the thickness 74. The embodiment shown in FIG. 9 has a ratio of about 5:1 between the first distance 110 and the thickness 74. This means that the first distance 110 has a value in a range from about two times to about five times the thickness 74 of the wave washer 68.

The medical instrument 10 depicted in FIGS. 1 to 7 has a connecting device 58 which is configured in the form of an applied connecting device 114. The applied connecting device 114 comprises one single first bearing area 52 and one single second bearing area 54. It is further configured such that the first part 12 with the single first bearing area 52 is applied to the single second bearing area 54 with the biasing element 56 arranged therebetween.

The embodiment of the wave washer 68 depicted in FIGS. 1 to 10 has five wave troughs 70 and five wave crests 72 and a corresponding number of five points of inflection 86 and five points of inflection 88 along the cutting line 84 as described above.

Figure 11:
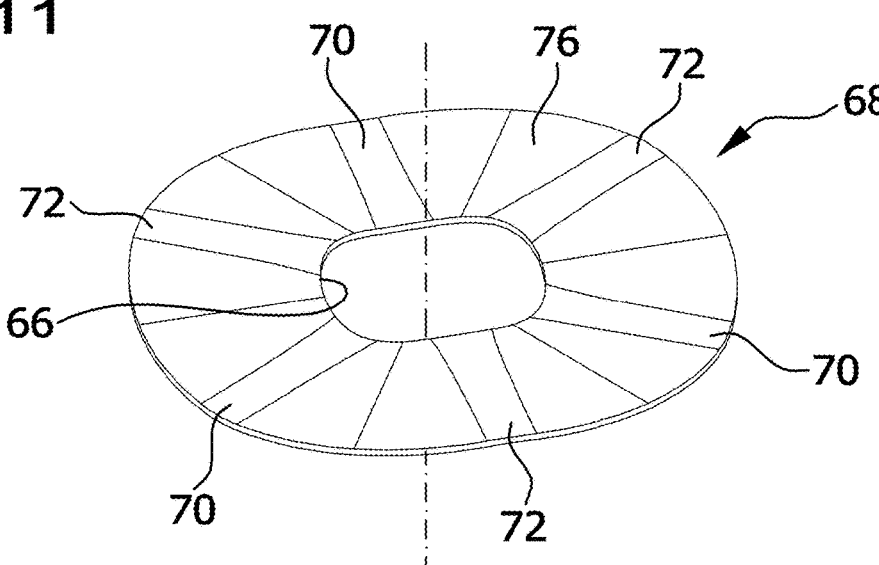
FIG. 11 shows a perspective view of a further embodiment of a wave washer.
Figure 12:
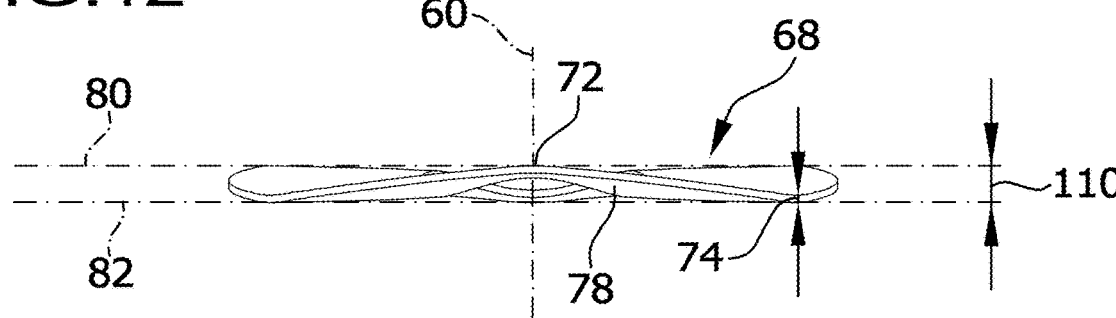
FIG. 12 shows a side view of the wave washer depicted in FIG. 11.
Figure 13:
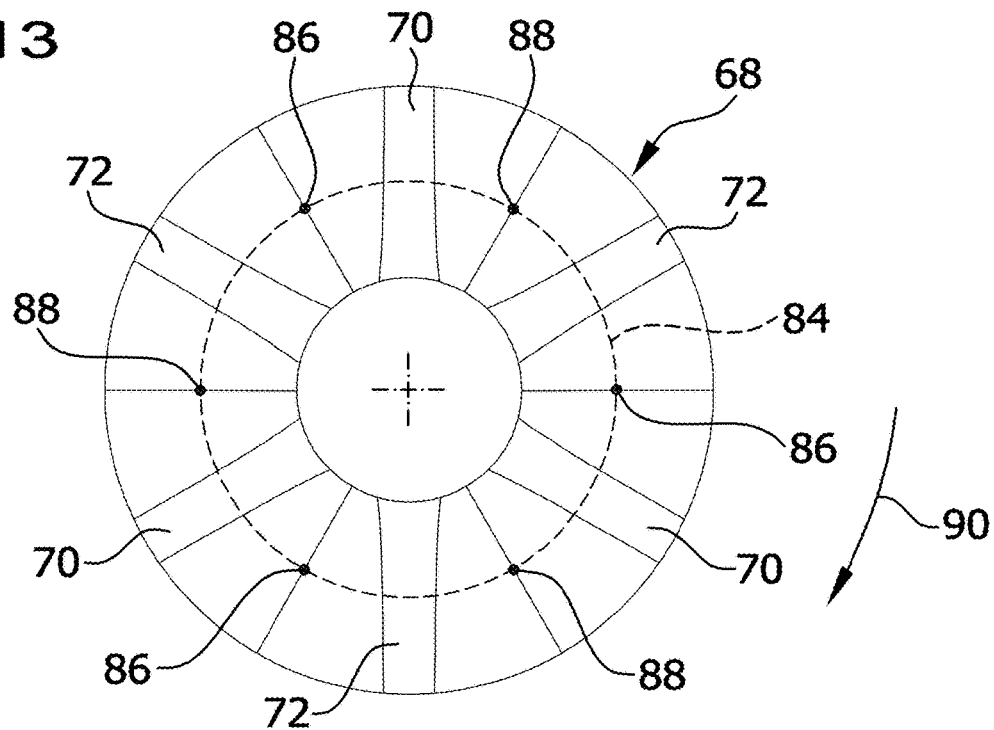
FIG. 13 shows a top view of the wave washer depicted in FIGS. 11 and 12.

FIGS. 11 to 13 show a further embodiment of a wave washer 68. The configuration of the wave washer 68 shown in FIGS. 11 to 13 is similar to the wave washer 68 depicted in FIGS. 1 to 10. Therefore, the same reference numerals are used for denoting identical or similar elements.

The main difference between the wave washer 68 depicted in FIGS. 11 to 13 and the wave washer 68 depicted in FIGS. 1 to 10 is the number of wave troughs 70 and wave crests 72. The embodiment shown in FIGS. 11 to 13 has only three wave troughs 70 and three wave crests 72. This leads to a corresponding number of points of inflection 86 and 88 along the cutting line 84, namely three points of inflection 86 and 88 each.

Figures 14, 15, 16:
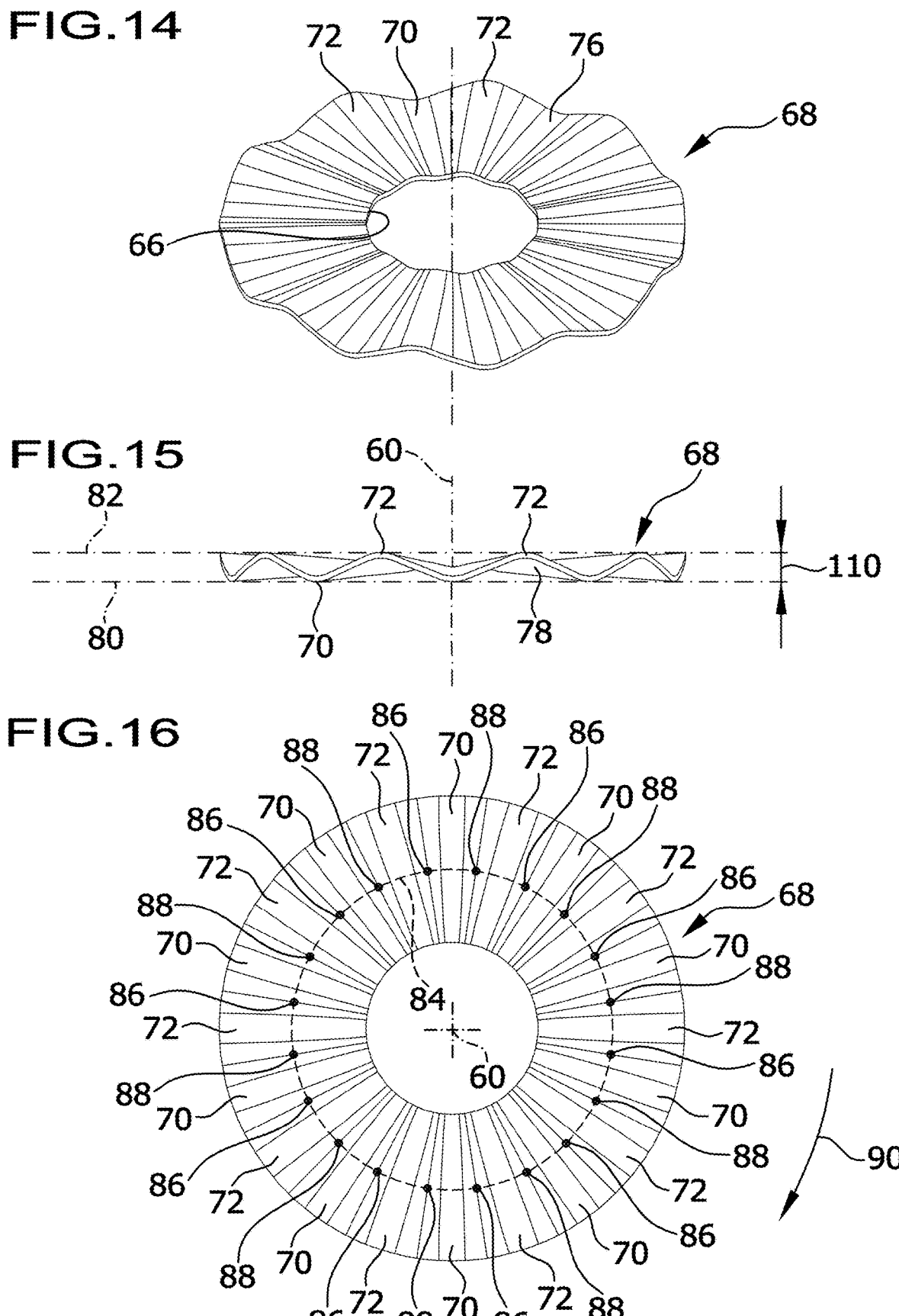
FIG. 14 shows a perspective view of a further embodiment of a wave washer.
FIG. 15 shows a side view of the wave washer depicted in FIG. 14.
FIG. 16 shows a top view of the wave washer depicted in FIGS. 14 and 15.

A further embodiment of a wave washer 68 is shown in FIGS. 14 to 16. Again, the same reference numerals are used for denoting identical or similar elements as for the embodiments shown in FIGS. 1 to 13.

The embodiment of the wave washer shown in FIGS. 14 to 16 differs from the embodiments described above again in the number of wave troughs 70 and wave crests 72. The embodiment shown in FIGS. 14 to 16 has ten wave troughs 70 and ten wave crests 72. This results in a corresponding number of ten points of inflection 86 and ten points of inflection 88 along cutting line 90 as described above.

Figure 17:
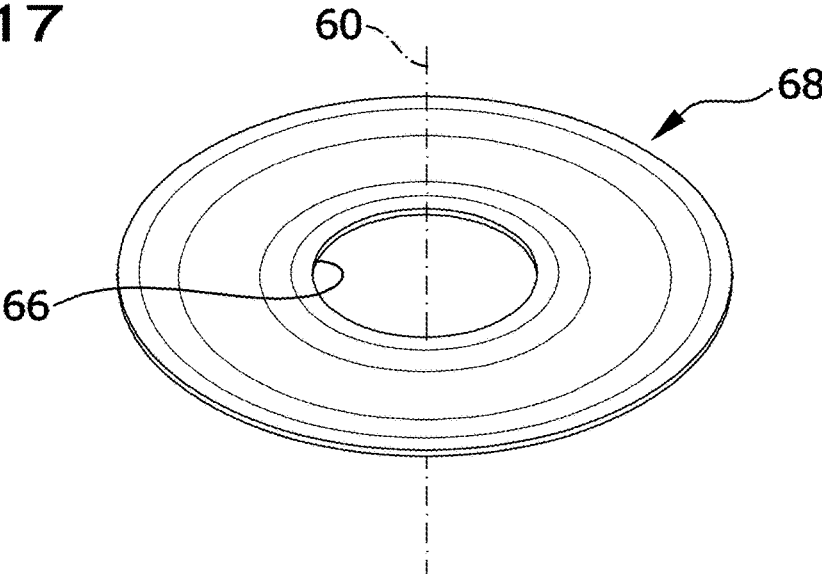
FIG. 17 shows a perspective view of a further embodiment of a wave washer.
Figure 18:
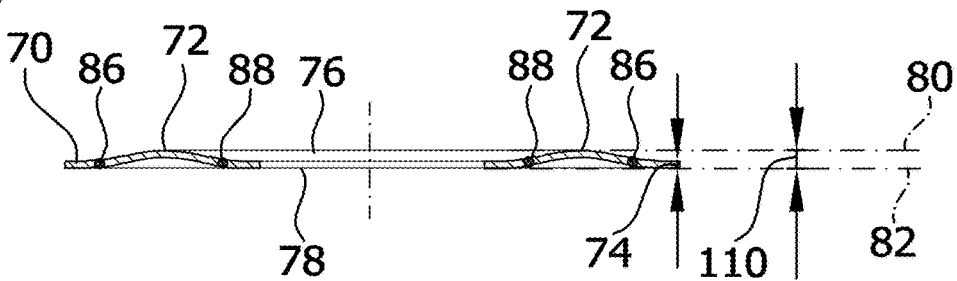
FIG. 18 shows a side view of the wave washer depicted in FIG. 17.
Figure 19:
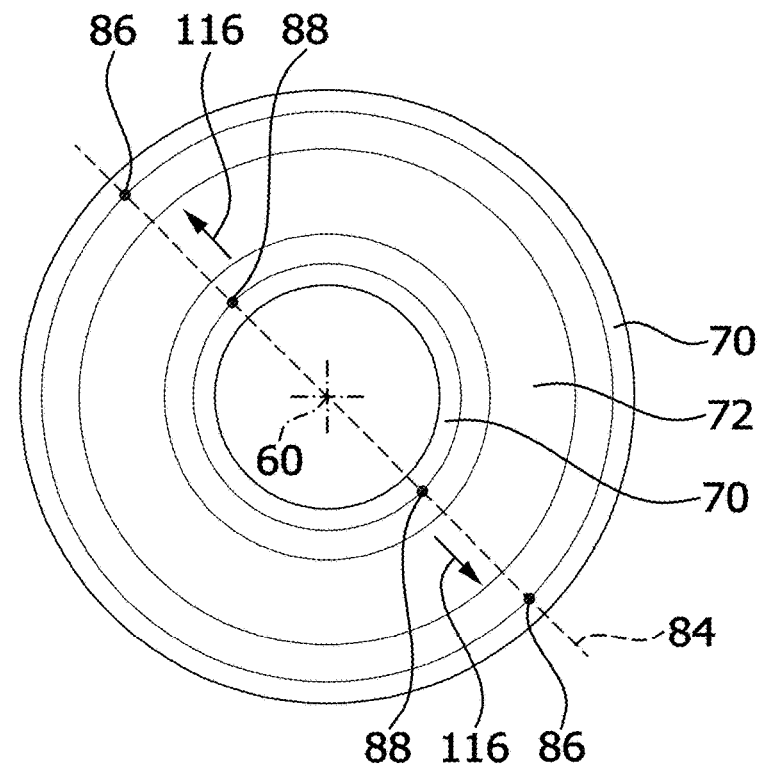
FIG. 19 shows a top view of the wave washer depicted in FIGS. 17 and 18.

FIGS. 17 to 19 show a further embodiment of a spring washer 68. The configuration of this spring washer 68 differs from the previously described spring washers in that the spring washer 68 undulates in a radial direction with respect to pivot axis 60. This results in a cutting line 84 in a radial direction 116 with respect to the pivot axis 60 having two points of inflection 86, 88. Starting from the pivot axis 60, a wave trough 70 is defined by an inner rim of the wave washer 68 surrounding the central opening 66. The concave curvature of wave trough 70 changes to a convex curvature at the point of inflection 88. Moving further away from the pivot axis 60 results in reaching the wave crest 72, and further moving from the wave crest 72 to the outer rim of the wave washer 68 defining a second wave trough 70 results in passing a second point of inflection 86 where the convex curvature changes to a concave curvature.

Figure 20:
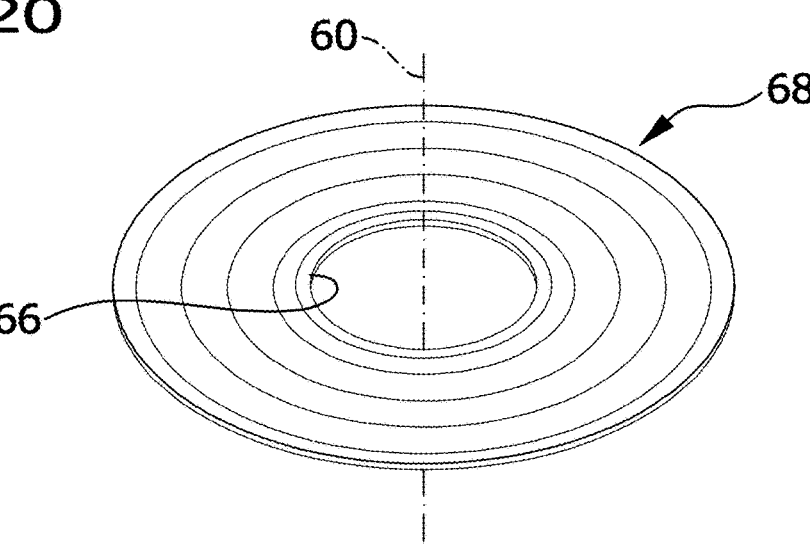
FIG. 20 shows a perspective view of a further embodiment of a wave washer.
Figure 21:
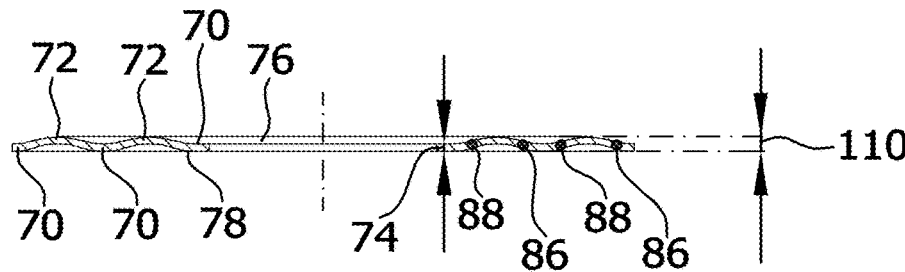
FIG. 21 shows a side view of the wave washer depicted in FIG. 20.
Figure 22:
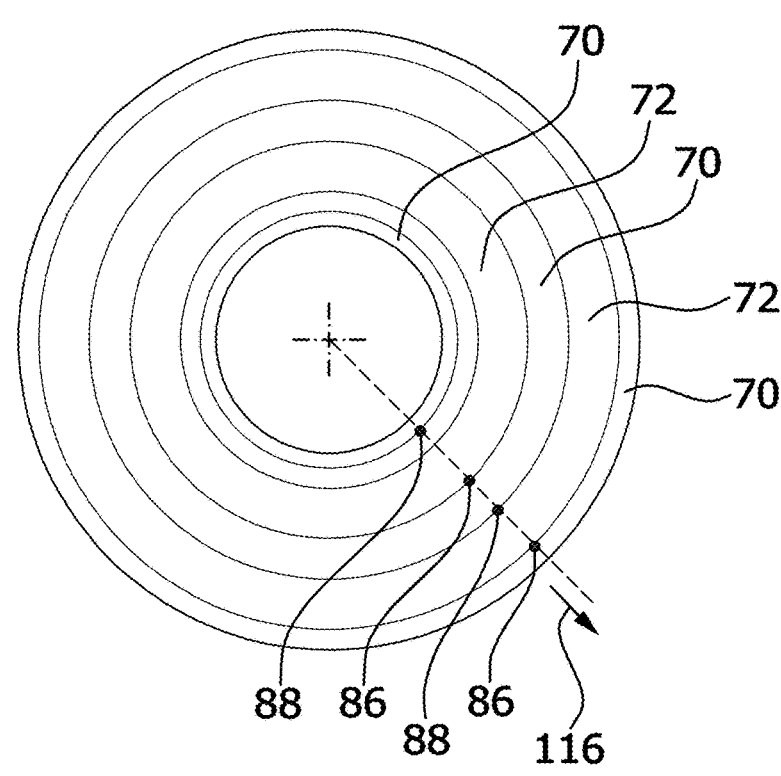
FIG. 22 shows a top view of the wave washer depicted in FIGS. 20 and 21.

Moreover, a further embodiment of a wave washer 68 is depicted in FIGS. 20 to 22. Again, reference numerals used for denoting identical or similar elements are used with respect to FIGS. 20 to 22 as in FIGS. 17 to 19.

This embodiment generally corresponds to the embodiment shown in FIGS. 17 to 19. This means that this wave washer 68 undulates in the radial direction 116 with respect to the pivot axis 60. This embodiment has three wave troughs 70 and two wave crests 72 starting with a wave trough 70 defined by an inner rim delimiting the central opening 86. An outer rim of the wave washer 68 defines a further wave trough 70.

Figure 23:
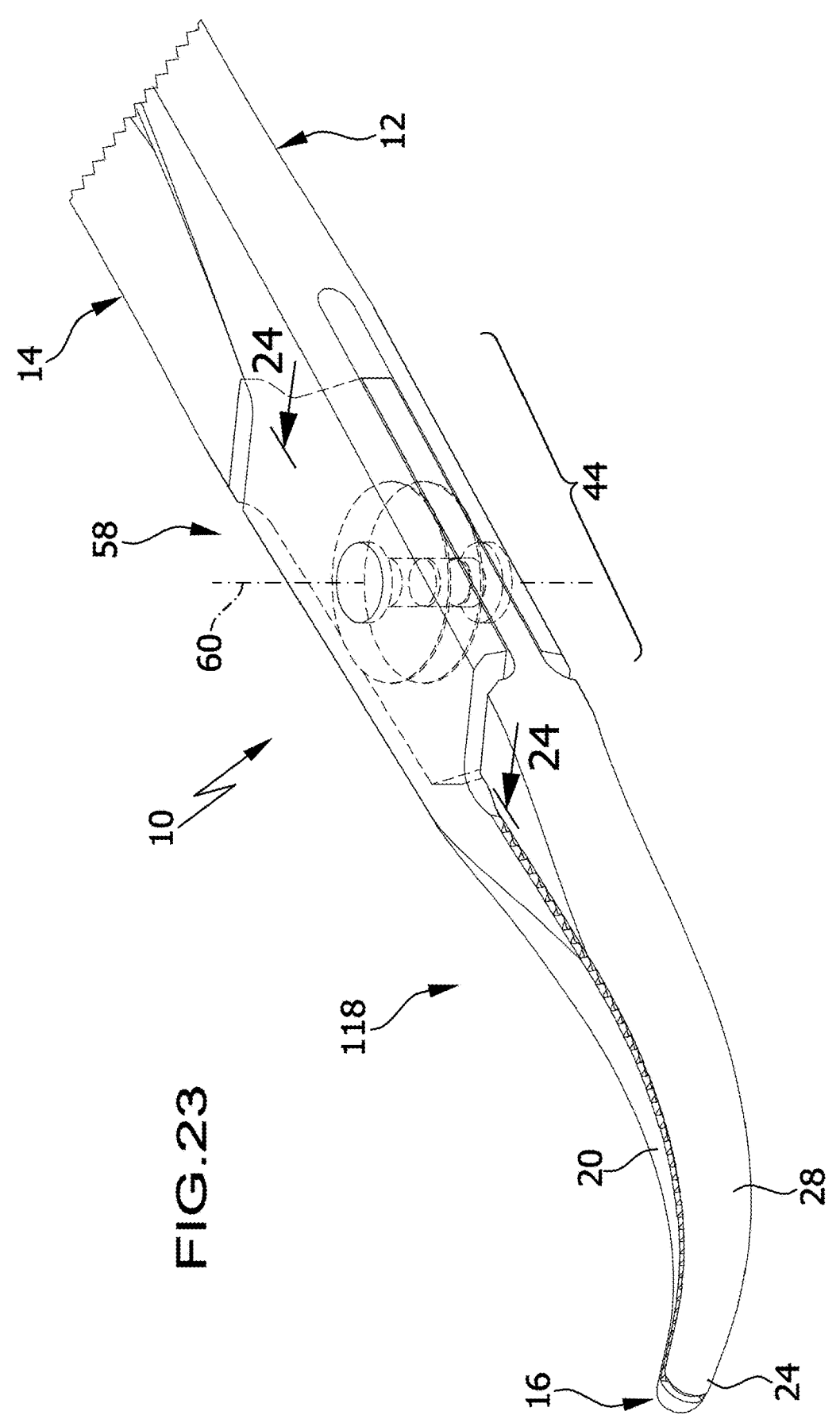
FIG. 23 shows a partially broken view of a portion of a further embodiment of a medical instrument with a box-type connecting device in the mounted state.
Figure 24:
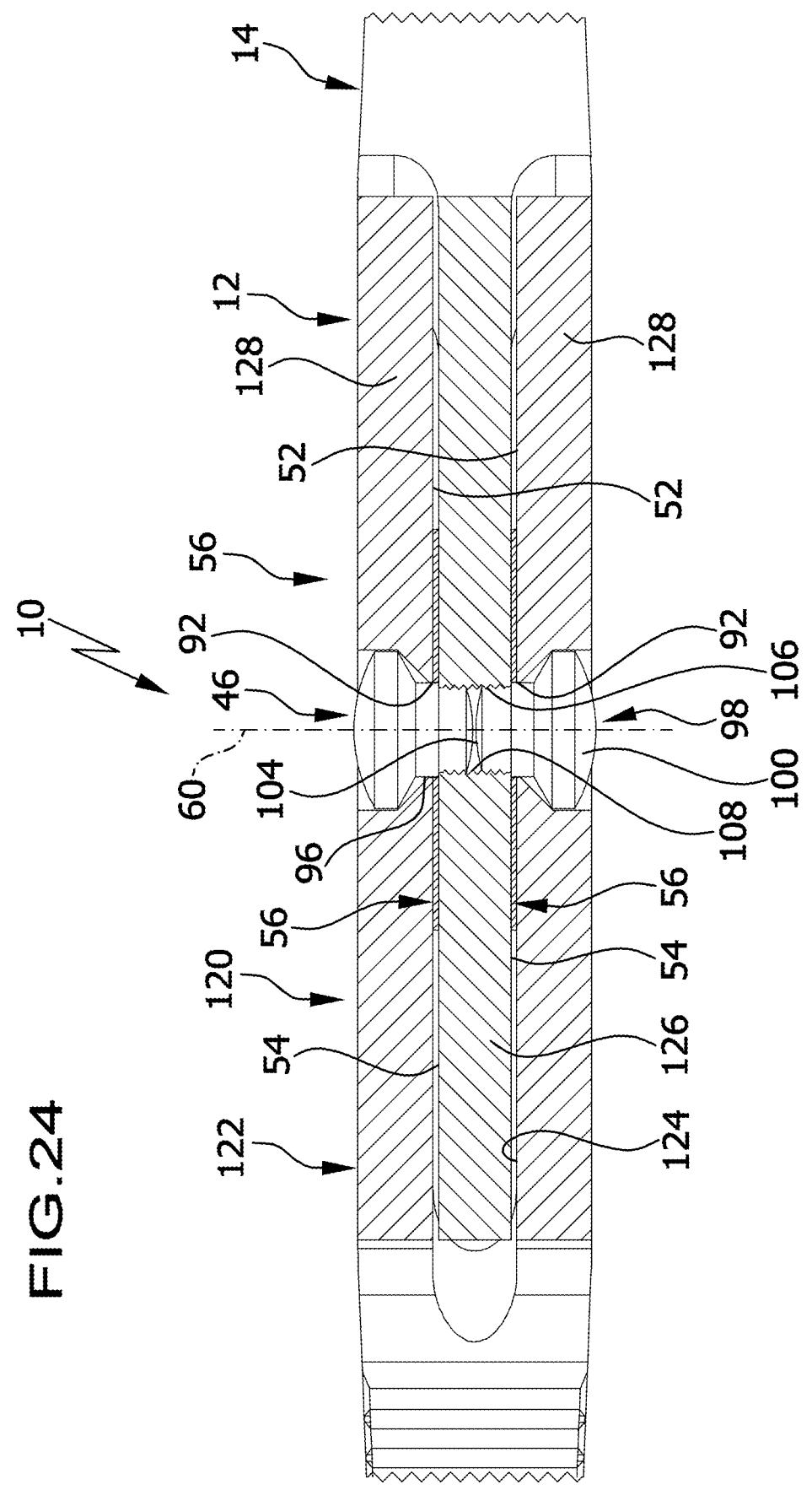
FIG. 24 shows a sectional view taken along line 24-24 in FIG. 23.

FIGS. 23 and 24 show a further embodiment of a medical instrument 10, namely a distal end region thereof. This instrument 10 is configured in the form of a needle holder 118. The tool elements 20 and 28 are curved with respect to a reference plane extending perpendicularly to the pivot axis 60.

The instrument 10 depicted in FIGS. 23 and 24 differs from the medical instrument depicted in FIGS. 1 to 7, in particular, in the different configuration of the connecting device 58. The instrument 10 shown in FIGS. 23 and 24 has a connecting device 58 which is configured in the form of a box-type connecting device 120.

The box-type connecting device 120 is characterized by the first part 12 having a female connecting portion 122 with a through opening 124. The second part 14 has a male connecting portion 126 which extends through the through opening 124 in the mounted state as shown in FIGS. 23 and 24. Due to this configuration, the female connecting portion 122 has two first bearing areas 52 facing each other. The male connecting portion 126 has two second bearing areas 54 facing away from one another. However, each first bearing area 52 faces a second bearing area 54.

Arranged between the respective first and second bearing areas 52, 54 is a biasing element 56. FIG. 24 shows the two biasing elements 56 in the compressed state, i.e. in the mounted or assembled state of the instrument 10.

The second part 14 is provided with a bore 106 coaxial with the pivot axis 60 and provided with inner threads 108.

Two connecting elements 46 in the form of connecting screws 98 are provided for connecting the first and second parts 12, 14 to one another. In an alternative embodiment, a rivet is provided for connecting the first and second parts 12, 14 to one another so as to form a so-called riveted boxlock with biasing elements 56.

The first part 12 comprises two bridges 128 delimiting the through opening 124 on both sides. Each bridge 128 is provided with a bore 92, which broadens away from the male connection portion 126 for receiving a screw head 100 of a connecting screw 98.

An unthreaded shaft portion 96 extends through the bore 92. A threaded shaft portion 102 extending between the shaft portion 96 and a free end 104 of the connecting screw 98 is provided with outer threads corresponding to the inner threads 108 of bore 106. This allows for screwing the connecting screws 98 into inner threads 108 of bore 106 with their respected shaft portion 102.

The described configuration of the connecting device 58 allows for individually compressing both biasing elements 56 between the respective first and second bearing areas 52, 54.

The medical instruments 10 described in connection with FIGS. 1 to 7 on the one hand and in connection with FIGS. 23 and 24 on the other hand can be provided with any of the above-described biasing elements 56 in the form of spring washers 64. Any of the described embodiments of wave washers 68 is suited to be placed between the first and second bearing area 52, 54 of the described instruments 10.

The described spring washers have a preferred thickness 74 in the range of about 0.05 mm to about 0.2 mm. As the instruments 10 have to be cleanable and sterilizable, the spring washers 64 are preferably made from stainless spring steel.

The biasing elements 65 described above can optionally be coated or provided with a hardened surface by an appropriate treatment, for example by diffusion hardening or blasting for obtaining an additional hardness to improve dry running properties of the biasing element 56.

As described above, the gaps defined by the wave troughs 70 and the wave crests 72 are closed or almost closed in the course of the assembly of the instrument 10 due to the compression of the biasing element so that the influence on the cleanability of the instrument 10 is rather limited.

Further, for avoiding increased friction between the first and second parts 12, 14 on the one hand and the biasing element 56 on the other hand, the biasing element 56 is preferably made from a material with an increased hardness or a reduced hardness compared to the material from which the first and second parts 12, 14 are made, so that there is a difference between the respective hardness of the first and second parts 12, 14 on the one hand and the biasing element 56 on the other hand.

The embodiments of the medical instruments 10 described above have, in particular, the advantageous property of maintaining a perceptible motion force, which is regarded as pleasant by surgeons, over their entire lifetime. Readjusting such instruments 10 is generally not necessary as the biasing element 56 maintains the motion force as desired even if the medical instrument 10 is subject to wear in the region of the connecting device 58.

Further, if the instrument 10 is damaged and requires repair and/or service, the biasing element 56 can easily be exchanged and the running surfaces do not require reworking, e.g. milling, grinding or polishing.

REFERENCE NUMERALS 10 medical instrument
12 first part
14 second part
16 first distal end
18 first proximal end
20 first tool element
22 first holding element
24 second distal end
26 second proximal end
28 second tool element
30 second holding element
32 medical tool
34 clamping jaw
36 clamping jaw
38 clamp
40 ring
42 ring
44 connecting region
46 connecting element
48 arm
50 arm
52 first bearing area
54 second bearing area
56 biasing element
58 connecting device
60 pivot axis
62 longitudinal axis
64 spring washer
66 central opening
68 wave washer
70 wave trough
72 wave crest
74 thickness
76 first surface
78 second surface
80 first contact plane
82 second contact plane
84 cutting line
86 point of inflection
88 point of inflection
90 clockwise direction
92 bore
94 region
96 shaft portion
98 connecting screw
100 screw head 102 shaft portion
104 end
106 bore
108 inner threads
110 first distance
112 second distance
114 applied connecting device
116 radial direction
118 needle holder
120 box-type connecting device
122 female connecting portion
124 through opening
126 male connecting portion
128 bridge

The invention claimed is:

1. A medical instrument comprising:
a first part;
a second part;
a connecting element; and
a biasing element,
the connecting element connecting the first part to the second part so that the first part and the second part are pivotable relative to one another about a pivot axis defined by a longitudinal axis of the connecting element,
the first part comprising at least one first bearing area,
the second part comprising at least one second bearing area,
the at least one first bearing area and the at least one second bearing area facing each other,
the biasing element, in a mounted state, being arranged between the at least one first bearing area and the at least one second bearing area,
the biasing element, in the mounted state, being held in a compressed state between the at least one first bearing area and the at least one second bearing area by the connecting element so as to exert a biasing force on the at least one first bearing area and the at least one second bearing area for keeping the at least one first bearing area and the at least one second bearing area biased away from one another and,
the medical instrument further comprising a connecting device, wherein the connecting device comprises a box-type connecting device, wherein the first part has a female connecting portion with a through opening, wherein the second part has a male connecting portion, and wherein the male connecting portion extends through the through opening in the mounted state.

2. The medical instrument according to claim 1, wherein:
the biasing element comprises a spring washer having a central opening for receiving the connecting element, and
the biasing element surrounds the pivot axis.

3. The medical instrument according to claim 2, wherein the spring washer is a wave washer.

4. The medical instrument according to claim 3, wherein the wave washer has a constant thickness.

5. The medical instrument according to claim 3, wherein the wave washer undulates:
a) in a circumferential direction with respect to the pivot axis;
or
b) in a radial direction with respect to the pivot axis.

6. The medical instrument according to claim 3, wherein the wave washer comprises a cutting line extending in a radial or circumferential direction with respect to the pivot axis, the cutting line having at least two points of inflection.

7. The medical instrument according to claim 3, wherein the wave washer has a wavelike shape defining at least one wave trough and at least one wave crest.

8. The medical instrument according to claim 7, wherein the at least one wave trough comprises a plurality of wave troughs, and at least one wave crest comprises a plurality of wave crests.

9. The medical instrument according to claim 8, wherein the wave washer comprises a first surface and a second surface, the first surface and the second surface facing in opposite directions, wherein the first surface defines a first contact plane of the plurality of wave crests, and wherein the second surface defines a second contact plane of the plurality of wave troughs.

10. The medical instrument according to claim 9, wherein the first contact plane and the second contact plane extend parallel to one another.

11. The medical instrument according to claim 10, wherein the first contact plane and the second contact plane extend parallel to one another in an initial state and/or in a mounted state.

12. The medical instrument according to claim 11, wherein:
the first contact plane and the second contact plane define a first distance from one another in the initial state,
the first contact plane and the second contact plane define a second distance from one another in the mounted state, in which the biasing element is mounted between the at least one first bearing area and the at least one second bearing area, and
the first distance is greater than the second distance.

13. The medical instrument according to claim 12, wherein:
a) in the mounted state, the second distance has a maximum value of about 1.2 times a thickness of the wave washer; and/or
b) in the initial state, the first distance has a value in a range from about 2 times the thickness of the wave washer to about 10 times the thickness of the wave washer.

14. The medical instrument according to claim 1, wherein the female connecting portion has two first bearing areas facing each other, and wherein the male connecting portion has two second bearing areas facing away from one another.

15. A method for manufacturing a medical instrument having a first part and a second part, the first part having at least one first bearing area, the second part having at least one second bearing area, the method comprising the steps of:
arranging the at least one first bearing area and the at least one second bearing area such that the at least one first bearing area and the at least one second bearing area face each other;
connecting the first part and the second part to one another with a connecting element such that the first part and the second part are pivotable relative to one another about a pivot axis defined by a longitudinal axis of the connecting element;
arranging a biasing element between the at least one first bearing area and the at least one second bearing area before connecting the first part and the second part to one another;
compressing the biasing element with the first part and the second part in a compressed state;
maintaining the compressed state by adjusting the connecting element such that the biasing element exerts a biasing force on the at least one first bearing area and the at least one second bearing area to keep the at least one first bearing area and the at least one second bearing area biased away from one another; and the medical instrument further comprising a connecting device, wherein the connecting device comprises a box-type connecting device, wherein the first part has a female connecting portion with a through opening, wherein the second part has a male connecting portion, and wherein the male connecting portion extends through the through opening in a mounted state.

16. The method for manufacturing a medical instrument according to claim 15, wherein the biasing element comprises a wave washer.

* * * * *